United States Patent [19]

Cromartie et al.

[11] Patent Number: 5,756,423
[45] Date of Patent: May 26, 1998

[54] METHOD OF CONTROLLING PLANTS BY INHIBITION OF FARNESYL PYROPHOSPHATE SYNTHASE

[75] Inventors: Thomas H. Cromartie, Albany; Karl J. Fisher, Petaluma, both of Calif.

[73] Assignee: Zeneca Limited, London, England

[21] Appl. No.: 889,960

[22] Filed: Jul. 10, 1997

Related U.S. Application Data

[63] Continuation of Ser. No. 619,123, Mar. 20, 1996, abandoned, which is a continuation of Ser. No. 259,085, Jun. 13, 1994, abandoned.

[51] Int. Cl.$^6$ .......................... A01N 25/00; A01N 43/80; C12Q 1/48; C12N 9/12
[52] U.S. Cl. .......................... 504/116; 504/271; 435/15; 435/193; 435/194
[58] Field of Search .......................... 504/116, 271; 435/15, 193, 194

[56] References Cited

U.S. PATENT DOCUMENTS 4,447,256  5/1984  Suzuki et al. .......................... 71/86

FOREIGN PATENT DOCUMENTS

| | | |
|---|---|---|
| 54-37829 | 3/1979 | Japan . |
| 55-98193 | 7/1980 | Japan . |
| 1508772 | 4/1978 | United Kingdom . |

OTHER PUBLICATIONS

Norman, M.A., Plant Physiol., "Site of Clomazone Action in Tolerant-Soybean and Susceptible-Cotton Photomixotrophic Cell Suspension Cultures," (1990), pp. 704–709.
Fisher et al. CA Abstract 123:144276. Abstract of PCT WO 95–10188, published Apr. 1995.
Bakuniak et al. CA Abstract 99:189788. Abstract of *J. Environ. Sci. Health, Part B*. B18(4–5):485–96. 1983.
Okamoto, Y. "Herbicide properties of aminophosphonic acid derivatives" *1st Internat'l Congress on Phosphorus Compounds*. Oct. 1977.
Croteau, Rodney. "Clomazone Does Not Inhibit the Conversion of Isopendenyl Pyrophosphate to Geranyl, Farnesyl, or Geranylgeranyl Pyrophosphate in Vitro", *Plant Physiology* 98:1515–1517. 1992.
Weimer, Monte, et al. "Herbicide Clomazone Does Not Inhibit In Vitro Geranylgeranyl Sythesis from Mevalonate", *Plant Physiology*, 98:427–432. 1992.
Kreuz, Klaus, et al. "The site of carotenogenic enzymes in chromoplasts from Narcissus pseudonarcissus L.", *Planta*, 154:66–69. 1982.

*Primary Examiner*—S. Mark Clardy
*Attorney, Agent, or Firm*—Melissa A. Shaw

[57] ABSTRACT

A method of controlling the growth of plants comprising applying to the locus of such plants an herbicidally effective amount of a compound exhibiting an $IC_{50}$ value of less than about 300 nM in the inhibition of farnesyl pyrophosphate synthase in daffodil chromoplasts.

2 Claims, No Drawings

METHOD OF CONTROLLING PLANTS BY INHIBITION OF FARNESYL PYROPHOSPHATE SYNTHASE

This application is a filed wrapper continuation of application Ser. No. 08/619,123, filed Mar. 20, 1996, abandoned, which is a file wrapper continuation of application Ser. No. 259,085, filed Jun. 13, 1994, now abandoned.

FIELD OF THE INVENTION

The present invention is directed to a method of controlling the growth of plants comprising applying to the locus of such plants an herbicidally effective amount of a compound exhibiting an $IC_{50}$ value of less than about 300 nM the inhibition of farnesyl pyrophosphate synthase in daffodil chromoplasts.

BACKGROUND OF THE INVENTION

Farnesyl pyrophosphate is known as an important plant intermediate in the biosynthesis of plant sterols, carotenoids and chlorophylls. In plants, farnesyl pyrophosphate is produced by the condensation of geranyl pyrophosphate with isopentenyl pyrophosphate. Geranyl pyrophosphate is itself produced by the reaction of dimethyl allyl pyrophosphate with isopentenyl pyrophosphate.

It has now been discovered that by applying to the locus of plants a herbicidally effective amount of a compound exhibiting an $IC_{50}$ value of less than about 300 nM in the inhibition of farnesyl pyrophosphate synthase in daffodil chromoplasts, the biosynthesis of farnesyl pyrophosphate is inhibited to such an extent that the growth of such plants effectively controlled.

U.S. Pat. No. 4,447,256 (Suzuki et al.) discloses certain herbicidal N-(unsubstituted or substitute pyridyl) aminomethylene-diphosphonic acids represented by the formula:

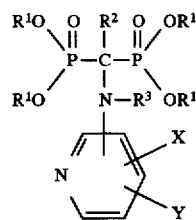

wherein each of $R^1$, $R^2$ and $R^3$ is independently hydrogen or lower alkyl, and each of X and Y is independently hydrogen, halogen, nitro, acetamino, carboxyl, lower alkyl, methoxycarbonyl, hydroxyl or methoxy, and salts thereof.

In addition, Japanese Patent Publication 54-37829 discloses herbicidal and fungicidal compounds having the structure

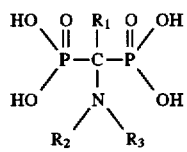

wherein $R_1$ is H, alkyl, alkenyl or —$CH_2COOC_2H_5$; $R_2$ is H, alkyl, alkenyl, benzyl or —$CH_2COOC_2H_5$; and $R_3$ is H, alkyl, alkenyl, cyclohexyl, cyclohexylmethyl, cyclopentyl, cycloheptyl, lower alkoxyalkyl, —$CH_2COOH$ or —$CH_2CH_2$—S—$C_2H_5$.

Somewhat similarly, Japanese Patent 55-98193 discloses, inter alia, the use of certain pyridine diphosphonic acids as herbicides having the structure:

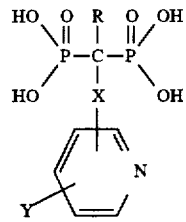

wherein X is $CH_2$, O or S; R is H, lower alkyl or halogen; and Y is H, lower alkyl or halogen.

While compounds of the above disclosures have been found to inhibit farnesyl pyrophosphate synthase in daffodil chromoplasts, 2-(2,2-diphosphonic acid)ethylpyridine having $IC_{50}$ value of 52 nM and certain of the compounds of Suzuki et al. and Nissan having lower values, it is noted that there is no indication in such publications that the observed control of plants was the result of this mode of action.

SUMMARY OF THE INVENTION

The present invention is directed to a method of controlling the growth of plants comprising applying to the locus of such plants an herbicidally effective amount of a compound exhibiting an $IC_{50}$ value of less than about 300 nM the inhibition of farnesyl pyrophosphate synthase in daffodil chromoplasts; with the provisos that said compound (a) is not of the formula:

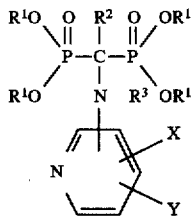

wherein each of $R^1$, $R^2$ and $R^3$ is independently hydrogen or lower alkyl, and each of X and Y is independently hydrogen, halogen, nitro, acetamino, carboxyl, lower alkyl, methoxycarbonyl, hydroxyl or methoxy, and salts thereof;

(b) is not of the formula

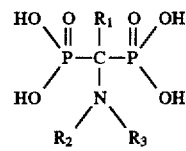

wherein $R_1$ is H, alkyl, alkenyl or —$CH_2COOC_2H_5$; $R_2$ is H, alkyl, alkenyl, benzyl or —$CH_2COOC_2H_5$; and $R_3$ is H, alkyl, alkenyl, cyclohexyl, cyclohexylmethyl, cyclopentyl, cycloheptyl, lower alkoxyalkyl, —$CH_2COOH$ or —$CH_2CH_2$—S—$C_2H_5$; and (c) is not of the formula:

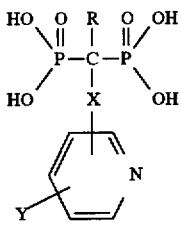

where X is CH$_2$, O or S; R is H, lower alkyl or halogen; and Y is H, lower alkyl or halogen.

DETAILED DESCRIPTION OF THE PREFERRED EMBODIMENTS

The method of the present invention involves controlling the growth of plants by applying to the locus of plants an herbicidally effective amount of a compound exhibiting an IC$_{50}$ value of less than about 300 nM in the inhibition of farnesyl pyrophosphate synthase in daffodil chromoplasts.

As is employed herein the term "control" is intended to denote the inhibitive control or modification of undesired plant growth. Inhibitive control and modification include all deviations from natural development such as, for example, total killing, growth retardation, defoliation, desiccation, albinism, regulation, stunting, tillering, stimulation, leaf burn and dwarfing. The term "herbicidally effective amount" is used to denote any amount which achieves such control or modification when applied to the undesired plants themselves or to the area in which these plants are growing. The term "plants" is intended to include germinated seeds, emerging seedlings and established vegetation, including both roots a above-ground portions.

The compounds employed in the practice of this invention possess an IC$_{50}$ value of less than about 300 nM in the inhibition of farnesyl pyrophosphate synthase in daffodil chloroplasts, and will preferably possess an IC$_{50}$ value of less than about 50 nM.

The IC$_{50}$ value may be determined as follows. Daffodil chromoplasts are diluted to a volume of 500 microliters in a buffer containing 0.5M sucrose, 3 mM MgCl$_2$, 1 mM ethylenediaminetetraacetic acid, 20 mM N-tris [hydroxymethyl]methyl-2-aminoethanesulfonic acid, 10 nM N-[2-hydroxyethyl]-piperazine-N'-[2-ethanesulfonic acid], 5 mM L-cysteine, 10 mM sodium fluoride, and 0.1% bovine serum albumin at pH 7.7. The inhibitor to be tested may be dissolved in water other suitable solvent and then added to the reaction mixture. The assay is started by the addition of $^{14}$C-labeled isopentenyl pyrophosphate (52 Ci/mol) to give a final concentration in the assay of about 3 micromolar. The mixture is incubated at 30° C. with gentle agitation for a period of about 30 min. The reaction may be stopped by the addition of 0.5 mL of saturated NaCl and 2 mL of n-butanol saturated with water. After thorough mixing, the turbid suspensions are centrifuged briefly to separate the layers, and 1 mL of the bright yellow upper butanol layer is added to 10 mL of a suitable scintillation fluid which gives a single phase. The butanol soluble radioactivity is then measured in a scintillation counter.

The counts per minute (cpm) value for each sample is partially quenched by the intense yellow color of the chromoplasts, but the extent of quenching does not seem to vary much within any single preparation of chromoplasts. In addition, the problem of variable quenching differences among different experiments can be essentially eliminated by determining the incorporation of radioactivity relative to controls. Each set of experiments requires two control tubes identical to the test samples except that they contain no inhibitor. One of these is quenched immediately (TO sample) and one is quenched at the end of the normal incubation period (T100 sample).

For each concentration of inhibitor examined the % residual activity is determined from the formula $$\% \text{ Residual Activity} = \frac{[cpm \text{ (sample)} - cpm \text{ (T0)}]}{[cpm \text{ (T100)} - cpm \text{ (T0)}]}$$

A plot of the % Residual Activity against the logarithm of the inhibitor concentration is constructed, and the best line is drawn through the data. The concentration which the % Residual Activity is approximately 50% is reported as the IC$_{50}$ value, the concentration at which the enzyme reaction is half as fast as in the absence of inhibitor.

The daffodil chloroplasts employed may be prepared accordance with the following procedure.

Tightly closed daffodil flowers (Narcissus pseudonarcissus) are allowed to open at room temperature. Chromoplasts from the inner coronae only are isolated by modification of the prodedure of B. Liedvogel, P. Sitte and H. Folk, Cytobiologie, 12(2), 155–174(1976). Coronae are placed in twice their weight of isolation buffer consisting of 67 mM potassium phosphate, 0.74M sucrose, 5 mM MgCl$_2$ and 0.2% polyvinylpyrrolidone at pH 7.6 and are disrupted by 30 seconds of homogenization at high speed in a Waring-type blender. The mixture is filtered through several layers of cheesecloth and 2 layers of 100 micron nylon mesh, and the resulting filtrate is centrifuged at 1000×g for 10 minutes. The pellet is discarded and the supernatant is centrifuged at 22,000×g for 2 minutes. The supernatant is discarded and the orange chromoplast pellet is gently resuspended with a loose fitting Potter-Elvehjem homogenizer in 67 mM potassium phosphate buffer at pH 7.6 containing 5 mM MgCl$_2$ and 45% (w/v) sucrose. About 20 mL of the resulting suspension is transferred to an ultracentrifuge tube and overlaid with a discontinuous sucrose gradient consisting of 7 mL of the same buffer containing 30% (w/v) sucrose and then again with 7 mL of the same buffer containing 15% (w/v) sucrose. Centrifugation at 50,000×g for one hour gives yellow bands at the 15/30% interface and the 30/45% interface and a gelatinous pellet at the bottom of the tube. The upper yellow bands are collected, combined, a diluted slowly with, initially, a potassium phosphate buffer at pH 7.6 containing 5 mM MgCl$_2$ and 15% (w/v) sucrose, and later with the same buffer without sucrose so that the final solution contains about 15% (w/v) sucrose. This solution is centrifuged at 22,000×g for 20 minutes to give orange pellets which are suspended in a buffer at 100 mM tris(hydroxymethyl) aminomethane at pH 7.6 containing 5mM MgCl$_2$ and 2 mM dithiothreitol (1 ml per 20 coronae). This solution may be frozen in liquid nitrogen and then stored at −80° C.

Several of the novel herbicides which have been found to exhibit such an inhibition of farnesyl pyrophosphate synthase, with a resulting effective control of plants, are among those aza bisphosphonic acid compounds described in the herbicidal composition of copending U.S. application Ser. No. 08/133,722 filed Oct. 7, 1993, the disclosure which is hereby incorporated by reference.

These compounds are of the structural formula

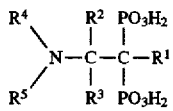

wherein $R^1$ is hydrogen, hydroxy, $C_1$–$C_4$ alkoxy, halogen, $C_1$–$C_4$ alkyl, $C_1$–$C_4$ haloalkyl, hydroxy-$C_1$–$C_4$-alkyl, hydroxy-$C_1$–$C_4$-alkoxy or $N(R^6)(R^7)$ wherein $R^6$ and $R^7$ are each independently hydrogen or $C_1$–$C_3$ alkyl;

$R^2$ and $R^3$ are each independently hydrogen; hydrocarbyl; substituted hydrocarbyl; hydrocarbyloxy; substituted hydrocarbyloxy; hydrocarbyl-$S(O)_m$—; or substituted hydrocarbyl-$S(O)_m$—; or $R^2$ and $R^3$ together form a 3–6 membered carbocyclic ring, optionally substituted with halogen, hydroxy, $C_1$–$C_6$ alkyl, $C_1$–$C_6$ alkoxy, $C_1$–$C_6$ alkylthio or $N(R^8)(R^9)$ wherein $R^8$ and $R^9$ are each independently hydrogen or $C_1$–$C_{12}$ alkyl; and $R^4$ and $R^5$ are each independently hydrogen; hydrocarbyl; substituted hydrocarbyl; hydrocarbyloxy; substituted hydrocarbyloxy; hydrocarbylthio; substituted hydrocarbylthio; pyridyl; substituted pyridyl; or are of the formula $N(R^{10})$—$(R^{11})$ wherein $R^{10}$ and $R^{11}$ are independently hydrogen, hydrocarbyl or substituted hydrocarbyl; or $R^4$ and $R^5$ together with the nitrogen to which they are bound form an aziridine, piperazine, morpholine, thiomorpholine, thiomorpholine sulfinyl, thiomorpholine sulfonyl, hexamethyleneimine, piperidine, tetrahydropyridine, pyrazole, imidazole, pyrrole, triazole, tetrahydropyrimidine, dihydroimidazole, pyrroline, azetidine, perhydroindole, perhydroquinoline, perhydroisoquinoline or pyrrolidine ring, any of which may be optionally substituted with $C_1$–$C_{12}$ alkyl, halo, $C_6$–$C_{10}$ aryl, $C_6$–$C_{10}$ aryl substituted with halo or $C_1$–$C_6$ alkyl, $C_7$–$C_{16}$ aralkyl, $C_7$–$C_{16}$ aralkyl substituted with halo or $C_1$–$C_6$ alkyl, nitro, halo-$C_1$–$C_{10}$-alkyl, $C_1$–$C_{10}$ alkoxy, $C_1$–$C_{10}$ alkylthio, $C_1$–$C_{10}$ alkylsulfonyl, phenoxy, phenoxy substituted with halo or $C_1$–$C_6$ alkyl, $C_1$–$C_{10}$ alkenyl or cyano; or $R^2$ and $R^4$ together with the nitrogen and carbon atoms to which they are bound form an aziridine, piperazine, morpholine, thiomorpholine, thiomorpholine sulfinyl, thiomorpholine sulfonyl, hexamethyleneimine, piperidine, tetrahydropyridine, pyrazole, imidazole, pyrrole, triazole, tetrahydropyrimidine, dihydroimidazole, pyrroline, azetidine, perhydroindole, perhydroquinoline, perhydroisoquinoline or pyrrolidine ring, any of which may be optionally substituted with $C_1$–$C_{12}$ alkyl, halo, $C_6$–$C_{10}$ aryl, $C_6$–$C_{10}$ aryl substituted with halo or $C_1$–$C_6$ alkyl, $C_7$–$C_{16}$ aralkyl, $C_7$–$C_{16}$ aralkyl substituted with halo or $C_1$–$C_6$ alkyl, nitro, halo-$C_1$–$C_{10}$-alkyl, $C_1$–$C_{10}$ alkoxy $C_1$–$C_{10}$ alkylthio, $C_1$–$C_6$ alkylsulfonyl, phenoxy, phenoxy substituted with halo or $C_1$–$C_6$ alkyl, $C_1$–$C_{10}$ alkenyl or cyano; and m is 0, 1 or 2;

and agrochemically acceptable salts thereof.

By employing the daffodil chloroplast test described above, one of skill in the art can easily determine other classes of molecules which possess sufficient farnesyl pyrophosphate synthase inhibitory effect to be employed in the practice of the present invention.

The compounds employed in the present invention are useful as herbicides and can be applied in a variety of way known to those skilled in the art, at various concentrations. The compounds are useful in controlling the growth of undesirable vegetation by application to the locus where control is desired. In practice, the compounds are applied as formulations containing the various adjuvants and carriers known to or used in the industry for facilitating dispersion. The choice of formulation and mode of application for any given compound may affect its activity, and selection will be made accordingly. The compounds of the invention may thus be formulated as wettable powders, as emulsifiable concentrates, as powders or dusts, as flowables, as solutions, suspensions or emulsions, or in controlled-release forms such as microcapsules. These formulations may contain as little as about 0.5% to as much as amount 95% or more by weight of active ingredient. The optimum amount for any given compound will depend upon the nature of plants to be controlled. The rate of application will generally vary from about 0.01 to about 10 pounds per acre, preferably from about 0.02 to about 4 pounds per acre.

Wettable powders are in the form of finely divided particles which disperse readily in water or other liquid carriers. The particles contain the active ingredient retained in a solid matrix. Typical solid matrices include fuller's earth, kaolin clays, silicas and other readily wet organic or inorganic solids. Wettable powders normally contain about 5% to about 95% of the active ingredient plus a small amount of wetting, dispersing, or emulsifying agent.

Emulsifiable concentrates are homogeneous liquid compositions dispersible in water or other liquid, and may consist entirely of the active compound with a liquid or solid emulsifying agent, or may also contain a liquid carrier, su as xylene, heavy aromatic naphthas, isophorone and other non-volatile organic solvents. In use, these concentrates are dispersed in water or other liquid and normally applied as spray to the area to be treated. The amount of active ingredient may range from about 0.5% to about 95% of the concentrate.

Dusts are free-flowing admixtures of the active ingredient with finely divided solids such as talc, clays, flours and other organic and inorganic solids which act as dispersants and carriers.

Microcapsules are typically droplets or solutions of the active material enclosed in an inert porous shell which allows escape of the enclosed material to the surroundings at controlled rates. Encapsulated droplet are typically about 1 to 50 microns in diameter. The enclosed material typically constitutes about 50 to 95% of the weight of the capsule, and may include solvent in addition to the active compound. Shell or membrane materials include natural and synthetic rubbers, cellulosic materials, styrene-butadiene copolymers, polyacrylonitriles, polyacrylates, polyesters, polyamides, polyureas, polyurethanes and starch xanthates.

Other useful formulations for herbicidal applications include simple solutions of the active ingredient in a solvent in which it is completely soluble at the desired concentration, such as water, acetone, alkylated naphthalenes, xylene and other organic solvents. Pressurized sprayers, wherein the active ingredient is dispersed in finely-divided form as a result of vaporization of a low boiling dispersant solvent carrier, may also be used.

Many of these formulations include wetting, dispersing or emulsifying agents. Examples are alkyl and alkylaryl sulfonates and sulfates and their salts; polyhydric alcohols; polyethoxylated alcohols; esters and fatty amines. These agents when used normally comprise from 0.1% to 15% by weight of the formulation.

Each of the above formulations can be prepared as package containing the herbicide together with other ingredients of the formulation (diluents, emulsifiers, surfactants etc.). The formulations can also be prepared by a tank mix method, in which the ingredients are obtained separately and combined at the grower site.

The compounds of the present invention are also useful when combined with other herbicides and/or defoliants, desiccants, growth inhibitors, and the like. These other materials typically comprise from about 5% to about 95% of the active ingredients in the formulations. These combinations frequently provide a higher level of effectiveness in controlling weeds and often provide results unattainable with separate formulations of the individual herbicides.

Examples of other herbicides, defoliants, desiccants and plant growth inhibitors with which the compounds of this invention can be combined are:

A. Benzo-2,1,3-thiadiazin-4-one-2,2-dioxides such a bentazone;

B. hormone herbicides, particularly the phenoxy alkanoic acids such as MCPA, MCPA-thioethyl, dichlorprop, 2,4,5-T, MCPB, 2,4-D, 2,4-DB, mecoprop, trichlopyr, fluroxypyr, clopyralid, and their derivatives (e.g. salts, esters and amides);

C. 1,3-dimethylpyrazole derivatives such as pyrazoxyfen, pyrazolate and benzofenap;

D. Dinitrophenols and their derivatives (e.g. acetates such as DNOC, dinoterb, dinoseb and its ester, dinoseb acetate;

E. dinitroaniline herbicides such as dinitramine, trifluralin, ethalfluralin, pendimethalin; and oryzalin;

F. arylurea herbicides such as diuron, flumeturon metoxuron, neburon, isoproturon, chlorotoluron, chloroxuron linuron, monolinuron, chlorobromuron, daimuron, and methabenzthiazuron;

G. phenylcarbamoyloxyphenylcarbamates such as phenmedipham and desmedipham;

H. 2-phenylpyridazin-3-ones such as chloridazon, and norflurazon;

I. uracil herbicides such as lenacil, bromacil and terbacil;

J. triazine herbicides such as atrazine, simazine, aziprotryne, cyanazine, prometryn, dimethametryn, simetryne, and terbutryn;

K. phosphorothioate herbicides such as piperophos, bensulide, and butamifos;

L. thiolcarbamate herbicides such as cycloate, vernolate, molinate, thiobencarb, butylate*, EPTC*, triallate, diallate, ethyl esprocarb, tiocarbazil, pyridate, and dimepiperate;

M. 1,2,4-triazin-5-one herbicides such as metamitron and metribuzin;

N. benzoic acid herbicides such as 2,3,6-TBA, dicamba and chloramben;

O. anilide herbicides such as pretilachlor, butachlor, the corresponding alachlor, the corresponding compound propachlor, propanil, metazachlor, metolachlor, acetochlor, and dimethachlor;

P. dihalobenzonitrile herbicides such as dichlobenil, bromoxynil and ioxynil;

Q. haloalkanoic herbicides such as dalapon, TCA and salts thereof;

R. diphenylether herbicides such as lactofen, fluroglycofen or salts or esters thereof, nitrofen, bifenox acifluorfen and salts and esters thereof, oxyfluorfen and fomesafen; chlornitrofen and chlomethoxyfen;

S. phenoxyphenoxypropionate herbicides such as diclofop and esters thereof such as the methyl ester, fluazifop and esters thereof, haloxyfop and esters thereof, quizalofop and esters thereof and fenoxaprop and esters thereof such as the ethyl ester;

T. cyclohexanedione herbicides such as alloxydim and salts thereof, sethoxydim, cycloxydim, sulcotrione, tralkoxydim, and clethodim;

U. sulfonyl urea herbicides such as chlorosulfuron, sulfometuron, metsulfuron and esters thereof; benzsulfuron and esters thereof such as the ester thereof methyl, DPX-M6313, chlorimuron and esters such as the ethyl ester thereof, pirimisulfuron and esters such as the methyl ester thereof DPX-LS300 and pyrazosulfuron;

V. imidazolidinone herbicides such as imazaquin, imazamethabenz, imazapyr and isopropylammonium salts, thereof, imazethapyr;

W. arylanilide herbicides such as flamprop and esters thereof, benzoylprop-ethyl, diflufenican;

X. amino acid herbicides such as glyphosate and gluyfosinate and their salts and esters, sulphosate, and bilanafos;

Y. organoarsenical herbicides such as MSMA;

Z. herbicidal amide derivative such as napropamide, propyzamide, carbetamide, tebutam, bromobutide, isoxaben, naproanilide, diphenamid, and naptalam;

AA. miscellaneous herbicides including ethofumesate, cinmethylin, difenzoquat and salts thereof such as the methyl sulfate salt, clomazone, oxadiazon, bromofenoxim, barban, tridiphane, (in the ratio 3:1) flurochloridone, quinchlorac and mefanacet;

BB. examples of useful contact herbicides include bipyridylium herbicides such as those in which the active entity is paraquat and those in which the active entity is diquat.

* These compounds are preferably employed in combination with a safener such as 2,2-dichloro-N,N-di-2-propenylacetamide (dichlormid).

These formulations can be applied to the areas where control is desired by conventional methods. Dust and liquid compositions, for example, can be applied by the use of power dusters, boom and hand sprayers and spray dusters. The formulations can also be applied from airplanes as a dust or a spray or by rope wick applications.

The following are examples of typical formulations.

| 5% dust: | 5 parts active compound |
| | 95 parts talc |
| 2% dust: | 2 parts active compound |
| | 1 part highly dispersed silicic acid |
| | 97 parts talc |

These dusts are formed by mixing the components then grinding the mixture to the desired particle size.

Wettable powders:

| 70%: | 70 parts active compound |
| | 5 parts sodium dibutylnaphthylsulfonate |
| | 3 parts naphthalenesulfonic acid/phenolsulfonic acid/formaldehyde condensate (3:2:1) |
| | 10 parts kaolin |
| | 12 parts Champagne chalk |
| 40%: | 40 parts active compound |
| | 5 parts sodium lignin sulfonate |
| | 1 part sodium dibutylnaphthalene sulfonic acid |
| | 54 parts silicic acid |
| 25%: | 25 parts active compound |
| | 4.5 parts calcium lignin sulfate |
| | 1.9 parts Champagne chalk/hydroxyethyl cellulose (1:1) |
| | 1.5 parts sodium dibutylnaphthalene sulfonate |
| | 19.5 silicic acid |
| | 19.5 parts Champagne chalk |
| | 28.1 parts kaolin |
| 25%: | 25 parts active compound |
| | 2.5 parts isooctylphenoxy-polyethylene-ethanol |
| | 1.7 parts Champagne chalk/hydroxyethyl cellulose (1:1) |

-continued

| | |
|---|---|
| 10%: | 8.3 parts sodium aluminum silicate<br>16.5 parts kieselguhr<br>46 parts kaolin<br>10 parts active compound<br>3 parts of a mixture of sodium salts of saturated fatty alcohol sulfates<br>5 parts naphthalenesulfonic acid/formaldehyde condensate<br>82 parts kaolin |

These wettable powders are prepared by intimately mixing the active compounds with the additives in suitable mixers, and grinding the resulting mixture in mills or rollers.

Emulsifiable concentrate:

| | |
|---|---|
| 25%: | 25 parts active substance<br>2.5 parts epoxidized vegetable oil<br>10 parts of an alkylarylsulfonate/fatty alcohol polyglycol ether mixture<br>5 parts dimethylformamide<br>57.5 parts xylene |

The amount of the present compositions which constitute a herbicidally effective amount depends upon the nature of the seeds or plants to be controlled. The rate of application of active ingredients varies from about 0.01 to about 25 pounds per acre, preferably about 0.10 to about 1.0 pounds per acre with the actual amount depending on the overall costs and the desired results. It will be readily apparent to one skilled in the art that compositions exhibiting lower herbicidal activity will require a higher dosage than more active compounds for the same degree of control.

EXAMPLES

The following examples are intended to further illustrate the present invention and are not intended to lime the scope of this invention in any manner whatsoever.

Several aza bisphosphonic acid compounds of the class described in copending United States Patent application were prepared, and their $IC_{50}$ values of the production of farnesyl pyrophosphate synthase in daffodil chromoplasts measured as follows:

1. Preparation and Purification of Chromoplasts

Tightly closed daffodil flowers (*Narcissus pseudonarcissus*) were allowed to open at room temperature. Chromoplasts from the inner coronae only were isolated by modification of the procedure of Liedvogel et al, *Cytobiologie*, 12(2), 155–174 (1976). Coronae were placed in twice their weight of isolation buffer consisting of 67 mM potassium phosphate, 0.74M sucrose, 5 mM $MgCl_2$, and 0.2% polyvinyl-pyrrolidone at pH 7.6 and were disrupted by 30 seconds of homogenization at high speed in a Waring-type blender. The mixture was filtered through several layers of cheesecloth and 2 layers of 100 micron nylon mesh, and the resulting filtrate was centrifuged at 1000×g for 10 minutes. The pellet was discarded and supernatant was centrifuged at 22,000×g for 20 minutes. The supernatant was discarded and the orange chromoplast pellet was gently resuspended with a loose-fitting Potter-Elvehjem homogenizer in 67 mM potassium phosphate buffer at pH 7.6 containing 5 mM $MgCl_2$ and 45% (w/v) sucrose. About 20 mL the resulting suspension was transferred to an ultracentrifuge tube and overlaid with a discontinuous sucrose gradient consisting of 7 mL of the same buffer containing 30% (w,(v) sucrose and then again with 7 mL of the same buffer containing 15% (w/v) sucrose. Centrifugation at 50.000×g for one hour gave yellow bands at the 15/30% interface and at the 30/45% interface and a gelatinous pellet at the bottom of the tube. The upper yellow bands were collected, combined, and diluted slowly with, initially, a potassium phosphate buffer at pH 7. containing 5 mM $MgCl_2$ and 15% (w/v) sucrose, and later with the same buffer without sucrose so that the final solution contained about 15% (w/v) sucrose. This solution was centrifuged at 22.000×g for 20 minutes to give orange pellets which were suspended in a buffer of 100 mM tris(hydroxymethyl) aminomethane at pH 7.6 containing 5mM $MgCl_2$ and 2 mM dithiothreitol (1 ml per 10 coronae). This solution was frozen in liquid nitrogen and then stored at −80° C.

2. Assay Procedure and Data Analysis

Thawed daffodil chromoplasts (100–150 microliters) were diluted to a final volume of 500 microliters in a buffer containing 0.5M sucrose, 3 mM $MgCl_2$, 1 mM ethylenediaminetetraacetic acid, 10 mM N-[2-hydroxyethyl] piperazine-$N^1$-[2-ethanesulfonic acid], 5 mM L-cysteine, 10 mM sodium fluoride, and 0.1% bovine serum albumin at pH 7.7. The inhibitor to be tested was dissolved in water or other suitable solvent and was added to the reaction mixture. The assay was started by the addition of $^{14}$C-labeled isopentenyl pyrophosphate (52 Ci/mol) to give a final concentration in the assay of about 3 micromolar. The mixture was incubated at 30° C. with gentle agitation for a period of about 30 minutes. The reaction was stopped by the addition of 0.5 mL of saturated NaCl and 2 mL of n-butanol saturated with water. After thorough mixing, the turbid suspensions were centrifuged briefly to separate the layers, and 1 mL of the bright yellow upper butanol layer was added to 10 mL of a suitable scintillation fluid which gave a single phase. The butanol soluble radioactivity was then measured in a scintillation counter. Each set of experiments required two control tubes identical to the test samples except that they contain no inhibitor. One of these was quenched immediately (T0 sample) and one was quenched at the end of the normal incubation period (T100 sample). For each concentration of inhibitor examined the % residual activity was determined from the formula $$\% \text{ Residual Activity} = \frac{[cpm\ (\text{sample}) - cpm\ (T0)]}{[cpm\ (T100) - cpm\ (T0)]}$$

A plot of the % Residual Activity against the logarithm of the inhibitor concentration was constructed, and the best line was drawn through the data. The concentration at which the % Residual Activity is 50% is reported as the $IC_{50}$ value, the concentration at which the enzyme reaction is half as fast as in the absence of inhibitor.

The results of such testing as well as the structures of the compounds tested are set forth in TABLE I below.

TABLE I $$\begin{array}{c} R^4 \quad R^2 \quad PO_3H_2 \\ \phantom{R^4}\backslash\phantom{xx}|\phantom{xxx}| \\ N-C-C-R^1 \\ \phantom{R^4}/\phantom{xx}|\phantom{xxx}| \\ R^5 \quad R^3 \quad PO_3H_2 \end{array}$$

| COMP. NO. | $R^1$ | $R^2$ | $R^3$ | $R^4$ | $R^5$ | $IC_{50}$ |
|---|---|---|---|---|---|---|
| 1. | H | H | H | \multicolumn{2}{c}{$-CH_2-CH_2-CH_2-CH_2-CH_2-$} | 32 |
| 2. | | | | \multicolumn{2}{c}{pyrrolidine with $-C(PO_3H_2)(OH)(PO_3H_2)$} | 933 |
| 3. | H | H | H | H | $-nC_3H_7$ | 30 |
| 4. | H | H | H | \multicolumn{2}{c}{$-CH_2-CH_2-CH_2-CH_2-$ trimethylsulfonium salt} | 38 |
| 5. | H | H | H | H | cyclohexyl | 425 |
| 6. | H | H | H | H | $-iC_3H_7$ | 89 |
| 7. | H | H | H | H | $-tC_4H_9$ | 238 |
| 8. | H | H | H | $-CH_3$ | $-CH_3$ | 2900 |
| 9. | | | | \multicolumn{2}{c}{piperidine with $-C(PO_3H_2)(OH)(PO_3H_2)$} | 209 |
| 10. | H | H | H | \multicolumn{2}{c}{$-CH(CH_3)-CH_2-CH_2-CH_2-CH_2-$} | 83 |
| 11. | H | H | H | \multicolumn{2}{c}{$-CH(CH_3)-CH_2-CH_2-CH(CH_3)-$} | 650 |
| 12. | H | H | H | H | $-iC_4H_9$ | 150 |
| 13. | H | H | H | $-C_2H_5$ | $-C_2H_5$ | 240 |
| 14. | H | H | H | H | $-nC_4H_9$ | 347 |
| 15. | H | H | H | H | $-OCH_3$ | 6310 |
| 16. | H | H | H | H | $-CH_2CH_2CH=CH_2$ | 316 |
| 17. | H | H | H | H | $-nC_6H_{13}$ | 316 |
| 18. | H | H | H | H | $-CH_2CH=CH_2$ | 26 |
| 19. | H | H | H | $-nC_3H_7$ | $-nC_3H_7$ | 32 |
| 20. | H | H | H | H | $-C_2H_5$ | 150 |
| 21. | H | H | H | \multicolumn{2}{c}{$-CH_2-CH(CH_3)-CH_2-CH_2-CH_2-$} | 385 |
| 22. | H | H | H | H | $C_2H_5-O-CH_2CH_2-$ | 1160 |
| 23. | $-OH$ | H | H | H | $-CH_3$ | 500,000 |
| 24. | H | H | H | $-nC_4H_9$ | $-nC_4H_9$ | 190 |
| 25. | H | H | H | H | $CH_3$ | 1679 |
| 26. | H | H | H | H | $-CH(CH_3)$-phenyl | 1429 |
| 27. | H | H | H | H | isopropyl-phenyl | 1230 |
| 28. | H | H | H | H | $-CH_2CH_2$-phenyl | 1413 |
| 29. | H | H | H | \multicolumn{2}{c}{$-CH_2-CH_2-CH_2-CH_2-CH_2-CH_2-$} | 360 |

TABLE I-continued $$\begin{array}{c} R^4 \quad R^2 \quad PO_3H_2 \\ N-C-C-R^1 \\ R^5 \quad R^3 \quad PO_3H_2 \end{array}$$

| COMP. NO. | R¹ | R² | R³ | R⁴ | R⁵ | IC₅₀ |
|---|---|---|---|---|---|---|
| 30. | H | H | H | \multicolumn{2}{c}{−CH₂−CH₂−CH(CH₃)−CH₂−CH₂−} | 266 |
| 31. | H | H | H | H | 2-methyl-pyridin-3-yl | 6600 |
| 32. | H | H | H | −CH₃ | -nC₃H₇ | 27 |
| 33. | H | H | H | −CH₃ | -iC₃H₇ | 178 |
| 34. | H | H | H | H | −CH₂−C(CH₃)=CH₂ | 31 |
| 35. | H | H | H | \multicolumn{2}{c}{−CH₂−CH(CH₃)−CH₂−CH(CH₃)−CH₂−} | 520 |
| 36. | H | H | H | H | 2,6-dichloro-4-(trifluoromethyl)phenyl | >500,000 |
| 37. | H | H | H | −CH₂−CH=CH₂ | −CH₂−CH=CH₂ | 53 |
| 38. | H | H | H | −C₂H₅ | -nC₃H₇ | 124 |
| 39. | H | H | H | H | −CH₂−CF₃ | 380 |
| 40. | H | H | H | −C₂H₅ | −CH₂−CH=CH₂ | 88 |
| 41. | H | H | H | −CH₃ | −CH₂−CH=CH₂ | 60 |
| 42. | H | H | H | H | cyclopropyl | 27 |
| 43. | H | H | H | \multicolumn{2}{c}{−CH(CH₃)−CH₂−CH₂−CH₂−} | 93 |
| 44. | H | H | H | H | −CH(CH₃)−(4-fluorophenyl) | 2512 |
| 45. | H | H | H | \multicolumn{2}{c}{−CH₂−CH=CH−CH₂−CH₂−} | 26 |
| 46. | H | H | H | H | indan-2-yl | 440 |
| 47. | H | H | H | \multicolumn{2}{c}{−CH₂−C(CH₃)₂−CH₂−CH₂−CH₂−} | 2282 |
| 48. | H | H | H | H | −C(CH₃)(CH₂CH₃) | 32 |
| 49. | H | H | H | H | indan-1-yl | 1730 |

TABLE I-continued $$\begin{array}{c} R^4 \quad R^2 \quad PO_3H_2 \\ \phantom{R^4}\backslash \phantom{R^2}|\phantom{PO_3H_2}| \\ N-C-C-R^1 \\ \phantom{R^5}/\phantom{R^3}|\phantom{PO_3H_2}| \\ R^5 \quad R^3 \quad PO_3H_2 \end{array}$$

| COMP. NO. | $R^1$ | $R^2$ | $R^3$ | $R^4$ | $R^5$ | $IC_{50}$ |
|---|---|---|---|---|---|---|
| 50. | H | H | H | H | CH₃-cyclopentyl | 232 |
| 51. | H | H | H | -nC₃H₇ | $CH_3$<br>$-CH_2-CH-CH_3$ | 91 |
| 52. | H | H | H | -nC₃H₇ | -nC₄H₉ | 87 |
| 53. | H | H | H |  | $C_2H_5$<br>$\|$<br>$-CH-CH_2-CH_2-CH_2-CH_2-$ | 112 |
| 54. | H | H | H | -nC₃H₇ | $O$<br>$\|\|$<br>$-CH_2CH_2COH$ | 479 |
| 55. | H | H | H | H | $-CH_2CH_2CH_2$ | 484 |
| 56. | H | H | H | H | $CH_3$<br>$\triangleright\!\!\!+\cdot H$<br>$C_2H_5$ | 32 |
| 57. | H | H | H | H | $CH_3\ CH_3$<br>$\|\ \ \|$<br>$-CH-CH-CH_2-CH_2-CH_2-$ | 96 |
| 58. | H | H | H |  | $CH_3$<br>$\|$<br>$-CH=N-C=CH-$ | 107 |
| 59. | H | H | H | -nC₃H₇ | -nC₆H₁₃ | 135 |
| 60. | H | H | H |  | $CH_3$<br>$\|$<br>$-N=CH-C=CH-$ | 1413 |
| 61. | H | H | H | -nC₃H₇ | $CH_3$<br>$\|$<br>$-CH_2CH_2-CH-CH_3$ | 1000 |
| 62. | H | H | H | -nC₃H₇ | -nC₅H₁₁ | 186 |
| 63. | H | H | H | H | cyclopropyl-Ph | 2089 |
| 64. | H | H | H |  | $-CH=N-CH=CH-$ | 69 |
| 65. | H | H | H |  | $-C=N-CH_2-CH_2-CH_2-$ bis NH₄ salt | 50 |
| 66. | H | H | H | H | $-CH_2-CH(OH)-CH_3$ hydrpochloride salt | 58 |

In order to test the correlation of the daffodil chloroplast farnesyl pyrophosphate synthase inhibition with the efficiency of the compounds in controlling plants, the compounds listed in the foregoing Table were tested for herbicidal activity by various methods and at various rates of application. The results of some of these tests are given below. Results obtained in herbicidal screening are affected by a number of factors including: the amount of sunlight, soil type, soil pH, temperature, humidity depth of planting, plant growth stage, application rate as well as many other factors. All testing procedures are administered with the least amount of variability possible. State of the art equipment and techniques are employed to enable the screening process to remain consistent and reliable.

Seeds of several different weed species were planted in sandy loam soil containing only trace organic matter. Propagules were sown in individuals rows using one species per row across the width of an aluminum flat (19.5×9.5×6 cm). The grass weeds planted were green foxtail (Setaria viridis) ("SETVI"), wild oat (Avena fatua) ("AVEFA"), barnyard grass (Enchinochloa crusgalli) ("ECHCG"). Broadleaf weeds utilized were wild mustard (Brassica kaber), also known as Sinapis arvensis, ("SINAR"), velvetleaf (Abutilon theophrasti) ("ABUTH") and morningglory (Ipomoea spp.) ("IPOSS"). Additionally, yellow nutsedge (Cyperus esculentus) ("CYPES"), nutlets were sown. Seeding depths ranged from 1.0 to 1.5 cm and plant densities ranged from 3 to 25 plants per row depending on individual plant species.

The flats were placed into a greenhouse and watered overhead by sprinkling. The greenhouse environmental systems provided the plants with natural and artificial (via metal halide lamps) lighting to attain 14 hours of light per day. Day and night temperatures were maintained at 29° and 21° C. respectively. The plants were grown for 10 to 12 days (or to the appropriate growth stage) prior to compound application. Grasses were sprayed at a 3 to 4 leaf stage and broadleaves at a 1 to 2 leaf stage. Yellow nutsedge was 5 to 7 cm tall at application.

Solutions of the test compounds were prepared by weighing out 18.8 and 74.7 mg for 1 and 4 kg/ha applications respectively, of the test compound into a 60 ml wide-mouth bottle, then dissolving the compound in 14.0 ml of deionized water containing 0.5% v/v Tween 20' (polyoxyethylene sorbitan monolaurate emulsifier) as a surfactant. Additional solvents, not exceeding 2 ml (15% of spray volume), were used if needed to dissolve the compound.

The plants were sprayed inside an enclosed linear spray table with the nozzle set at 30.5 cm (12 inches) above the foliage.

The application rate was 4.0 kg/ha or 1.0 kg/ha (as indicated in Table III below). Treated plants were then returned to a greenhouse and watered daily without wetting the foliage.

The degree of weed control was evaluated 17–21 days after application and recorded as percentage of control as compared to the growth of the same species in an untreated control flat of the same. Percent control is the total injury to the plants due to all factors including: inhibited emergence, stunting, malformation, chlorosis and other types of plant injury. The control ratings range from 0 to 100 percent, where 0% represents no effect with growth equal to the untreated control and where 100% represents complete kill.

The results of such testing are presented in TABLE II below. A dash indicates that no test was performed at that level of application.

TABLE II

| | | Post-Emergent - Testin (4.0 kg/ha) | | | | | | |
|---|---|---|---|---|---|---|---|---|
| COMP. NO. | $IC_{50}$ | AVEFA | ECHCG | SETVI | ABUTH | IPOSS | SINAR | CYPES |
| 1. | 32 | 100 | 100 | 100 | 70 | 100 | 100 | 20 |
| 2. | 933 | 0 | 0 | 60 | 0 | 0 | 90 | 5 |
| 3.* | 30 | 100 | 100 | 100 | 70 | 95 | 100 | 30 |
| 4.* | 38 | 60 | 90 | 100 | 20 | 20 | 100 | 5 |
| 5. | 425 | 98 | 98 | 98 | 60 | 60 | 100 | 10 |
| 6. | 89 | 50 | 60 | 60 | 15 | 70 | 100 | 25 |
| 7. | 239 | 85 | 50 | 60 | 5 | 60 | 100 | 15 |
| 8. | 2900 | 5 | 5 | 50 | 0 | 5 | 85 | 0 |
| 9. | 209 | 60 | 30 | 100 | 30 | 30 | 100 | 15 |
| 10. | 83 | 100 | 85 | 85 | 50 | 90 | 100 | 5 |
| 11. | 610 | 30 | 50 | 50 | 0 | 30 | 95 | 0 |
| 12. | 150 | 100 | 98 | 98 | 98 | 90 | 100 | 70 |
| 13.* | 240 | 40 | 40 | 80 | 15 | 10 | 95 | 5 |
| 14* | 347 | 70 | 90 | 95 | 20 | 10 | 85 | 15 |
| 15.* | 6310 | 0 | 0 | 0 | 0 | 0 | 0 | 0 |
| 16.* | 316 | 80 | 100 | 90 | 10 | 10 | 100 | 20 |
| 17.* | 316 | 75 | 50 | 60 | 0 | 10 | 50 | 0 |
| 18.* | 26 | 100 | 98 | 98 | 30 | 70 | 100 | 50 |
| 19.* | 32 | 100 | 100 | 98 | 100 | 60 | 100 | 10 |
| 20.* | 150 | 40 | 60 | 50 | 0 | 0 | 10 | 15 |
| 21.* | 385 | 50 | 30 | 50 | 0 | 10 | 30 | 5 |
| 22.* | 1660 | 0 | 15 | 20 | 5 | 5 | 40 | 0 |
| 23. | >500,000 | 0 | 0 | 0 | 0 | 0 | 0 | 0 |
| 24.* | 190 | 98 | 98 | 85 | 0 | 5 | 30 | 10 |
| 25.* | 1679 | 100 | 100 | 100 | 98 | 90 | 100 | 85 |
| 26.* | 1429 | 80 | 80 | 60 | 20 | 10 | 40 | 5 |
| 27.* | 1230 | 80 | 90 | 90 | 75 | 5 | 100 | 75 |
| 28.* | 1413 | 60 | 5 | 30 | 5 | 5 | 50 | 10 |
| 29.* | 360 | 60 | 60 | 60 | 0 | 15 | 85 | 0 |
| 30.* | 266 | 90 | 90 | 95 | 5 | 30 | 100 | 5 |
| 31. | 6600 | 0 | 0 | 0 | 0 | 0 | 0 | 0 |
| 32.* | 27 | 100 | 95 | 100 | 75 | 85 | 100 | 25 |
| 33.* | 178 | 100 | 100 | 95 | 50 | 65 | 100 | 10 |
| 34.* | 31 | 95 | 95 | 95 | 60 | 60 | 100 | 15 |
| 35.* | 520 | 98 | 15 | 50 | 0 | 30 | 25 | 0 |
| 36. | >500,000 | 0 | 0 | 0 | 0 | 0 | 0 | 0 |
| 37.* | 53 | 95 | 95 | 100 | 10 | 15 | 98 | 10 |
| 38.* | 124 | 100 | 100 | 100 | 70 | 90 | 100 | 10 |
| 39.* | 380 | 20 | 0 | 5 | 0 | 0 | 0 | 0 |
| 40.* | 88 | 85 | 90 | 80 | 10 | 10 | 95 | 10 |
| 41.* | 60 | 100 | 95 | 95 | 85 | 85 | 100 | 60 |
| 42.* | 27 | 100 | 95 | 95 | 10 | 90 | 100 | 20 |
| 43.* | 93 | 100 | 98 | 98 | 30 | 60 | 100 | 5 |
| 44.* | 2512 | 90 | 100 | 100 | 60 | 10 | 90 | 60 |
| 45.* | 26 | 100 | 100 | 100 | 90 | 100 | 100 | 50 |
| 46.* | 440 | 50 | 15 | 20 | 5 | 0 | 5 | 10 |
| 47.* | 2282 | 0 | 0 | 10 | 0 | 0 | 5 | 0 |
| 48.* | 32 | 100 | 98 | 95 | 60 | 95 | 100 | 50 |
| 49.* | 1730 | 60 | 50 | 15 | 5 | 10 | 10 | 10 |
| 50.* | 232 | 50 | 60 | 85 | 5 | 5 | 85 | 5 |
| 51.* | 91 | 100 | 98 | 98 | 70 | 15 | 100 | 5 |

TABLE II-continued

Post-Emergent - Testin (4.0 kg/ha)

| COMP. NO. | IC$_{50}$ | AVEFA | ECHCG | SETVI | ABUTH | IPOSS | SINAR | CYPES |
|---|---|---|---|---|---|---|---|---|
| 52.* | 87 | 100 | 100 | 100 | 75 | 20 | 100 | 20 |
| 53.* | 112 | 98 | 100 | 98 | 70 | 30 | 90 | 5 |
| 54.* | 479 | 0 | 0 | 10 | 0 | 5 | 10 | 0 |
| 55.* | 484 | 75 | 80 | 100 | 60 | 10 | 100 | 30 |
| 56.* | 32 | 100 | 100 | 100 | 95 | 98 | 100 | 60 |
| 57.* | 96 | 100 | 100 | 100 | 80 | 90 | 100 | 15 |
| 58.* | 107 | 100 | 98 | 100 | 98 | 90 | 100 | 10 |
| 59.* | 135 | 85 | 90 | 95 | 30 | 20 | 90 | 5 |
| 60.* | 1413 | 10 | 30 | 30 | 10 | 5 | 20 | 0 |
| 61.* | 1000 | 100 | 100 | 90 | 70 | 30 | 90 | 10 |
| 62.* | 186 | 100 | 85 | 95 | 15 | 30 | 85 | 10 |
| 63.* | 2089 | 0 | 5 | 10 | 20 | 5 | 10 | 0 |
| 64.* | 69 | 100 | 98 | 100 | 75 | 100 | 100 | 30 |
| 65.* | 50 | 95 | 100 | 100 | 100 | 100 | 100 | 5 |
| 66.* | 58 | 90 | 95 | 98 | 90 | 75 | 100 | 60 |

*Tested a.t 1.0 kg/ha

The above data show the herbicidal efficacy of the farnesyl pyrophosphate synthase-inhibitor compounds employed in the practice of the present invention.

What is claimed is:

1. A method of assessing the herbicidal activity of a compound comprising measuring the IC$_{50}$ value of the compound in the inhibition of farnesyl pyrophosphate synthase.

2. A method according to claim 1, wherein the measuring of the IC$_{50}$ value of the compound comprises measuring the inhibition of the production of farnesyl pyrophosphate synthase in daffodil chromoplasts.